United States Patent [19]

Simon

[11] Patent Number: 5,919,760
[45] Date of Patent: Jul. 6, 1999

[54] METHOD FOR TREATING ACUTE AND SEVERE DIARRHEA

[75] Inventor: David Lew Simon, Mansfield Center, Conn.

[73] Assignee: Intensive Narcotic Detoxification Centers of America, LLC, Tolland, Conn.

[21] Appl. No.: 08/881,478

[22] Filed: Jun. 24, 1997

Related U.S. Application Data

[63] Continuation-in-part of application No. 08/631,081, Apr. 12, 1996, Pat. No. 5,783,583.
[51] Int. Cl.⁶ .......................... A61K 38/12; A01N 43/42; A01N 43/46
[52] U.S. Cl. ............................ 514/11; 514/281; 514/282; 514/424; 514/812; 514/867
[58] Field of Search .............................. 514/11, 282, 281, 514/424

[56] References Cited

U.S. PATENT DOCUMENTS

| | | | |
|---|---|---|---|
| 3,896,226 | 7/1975 | Fishman | 424/260 |
| 4,535,157 | 8/1985 | Meltzer et al. | 546/44 |
| 4,987,136 | 1/1991 | Krook et al. | 514/282 |
| 5,272,149 | 12/1993 | Stalling | 514/255 |
| 5,789,411 | 8/1998 | Gooberman et al. | 514/255 |

OTHER PUBLICATIONS

Gerra et al., "Clonidine and Opiate Receptor Antagonists in the Treatment of Heroin Addiction". Journal of Substance Abuse Treatment, vol. 12, No. 1. pp. 35–41. 1995.
Loimer et al., "Continuous Naloxone Administration Suppresses Opiate Withdrawal Symptoms In Huamn Opiate Addicts During Detoxification Treatment". 1989 pp. 81–86.
Text—*Opioid Peptides in Substance Abuse* by Jozsef I. Szekely. CRC Press, Inc., p. 160 (1994).
Article—Spanagel et al.—"Opposing tonically active endogenous opioid systems modulate the mesolimbic dopaminergic pathway" *Proc. Natl. Acad. Sci. USA* vol. 89. p. 2046. Mar. 1992.
Article—Pan et al. "Cellular mechanism for anti–analgesic action of agonists of the k–opioid receptor" *Nature* vol. 389/25 Sep., pp. 382–385.
Article—Kreeks et al. "Orally Administered opioid antagonists reverse both mu and kappa opioid agonists delay of gastrointestinal transit in the guinea pig" *Life Sciences*, vol. 56. No. 14. pp. 1187–1192. 1995.
Article—Arts et al. "Inhibition of the Antianalgesic Action of Dynorphin A in Mice by Cholera Toxin" *Pharacology Biochemistry and Behavior*, vol. 46. pp. 623–629. 1993.

Article—Bakashi et al. "Dynorphin A–(1–17) Induces Alterations in Free Fatty Acids, Excitatory Amino Acids, and Motor Function Through An Opiate–Receptor–Mediated Mechanism" *The Journal of Neuroscience,* Dec. 1990. 10(12):3793–3800.
Article—Behrmann et al. "A Comparison of YM–14673. U–50488H, and Nalmefene after Spinal Cord Injury in the Rat" *Experimental Neurology* 119. 258–267 (1993).
Article—Ohnishi et al. "Aquaretic Effect of the Stable Dynorphin–A analog E2078 in the Human" *The Journal of Pharmacology and Experimental Therapeutics* vol. 270. No. 1. Mar. 19, 1994.
Article——Salas et al. "[N–Methyl–Tyr⁴–N–Methyl–Arg⁷–D–LCU⁸]—Dynorphin–A–(1–8)Ethylamide, a Stable Dynorphin Analog. Produces Diuresis by Kappa–Opiate Receptor Activation in the Rat" *The Journal of Pharmacology and Experimental Therapeutics* vol. 262. No. 3. 1992.
Article—Wang et al. "Contribution of Alpha–2 adrenoceptors to Kappa Opioid Agonist–Induced Water Diuresis in the Rat" *The Journal of Pharmacology and Experimental Therapautics* vol. 270. 1994.
Article—O'Connor et al. Rapid and Ultrarapid Opioid Detoxification Techniques *JAMA*. Jan. 21. 1998—vol. 279, No. 3.
Partridge et al., "Pulmonary Edema Following Low–dose Naloxone Administration". Anesthesiology. vol. 65. No. 6. pp. 709–710. 1986.
Taff. "Pulmonary Edema Following Naloxone Administration in a Patient Without Heart Disease". Anesthesiology. 59. 576–77. 1983.
San et al. "High Risk of Ultrashort Noninvasive Opiate Detoxification". Am. J. Psychiatry 152. p. 956. Jun. 1995.
Brewer. C., Ultra–rapid, antagonist–precipitated opiate detoxification under general anesthesia or sedation. Addiction Biology 2/3. pp. 291–302. 1997.

*Primary Examiner*—Dwayne C. Jones
*Attorney, Agent, or Firm*—Cummings & Lockwood

[57] ABSTRACT

The invention provides a method for treating acute and severe diarrhea such as that which accompanies chemotherapy and rapid narcotic detoxification. The method includes administering octreotide in an amount sufficient to alleviate the diarrhea without precipitating clinically significant bradycardia. In a preferred embodiment an anticholenergic is administered together with octreotide to further reduce the possibility of significant bradycardia. The invention also provides a method for rapidly detoxifying a patient addicted to narcotics. Acute and severe diarrhea is eliminated during detoxification by administering octreotide in according to the above-described method.

16 Claims, No Drawings

5,919,760

METHOD FOR TREATING ACUTE AND SEVERE DIARRHEA

RELATED APPLICATIONS

This is a continuation-in-part of application Ser. No. 08/631,081 filed on Apr. 12, 1996 now U.S. Pat. No. 5,783,583

FIELD OF THE INVENTION

The present invention relates generally to a method for treating acute and severe diarrhea as may occur during chemotherapy or acute narcotic withdrawal. More particularly, the present invention provides such a method utilizing the somatostatin analogue octreotide.

BACKGROUND OF THE INVENTION

Acute and severe diarrhea may occur in many circumstances. However clinically significant diarrhea is commonly seen during cancer chemotherapy and during the acute phase of withdrawal in persons addicted to narcotics such as heroin and methadone.

Newer techniques for treating narcotic addiction entail purposefully precipitating an acute withdrawal reaction by the administration of narcotic antagonist drugs such as naloxone, naltrexone or nalmefene. For example, the '081 application, herein incorporated by reference, discloses rapid detoxification methods using the opioid antagonist nalmefene. As disclosed in the '081 application, the addicted patient is given a 1.0 mg intravenous bolus of nalmefene, followed by an intravenous infusion of 1.0 mg nalmefene some time after the initial bolus. Approximately 10 hours after the nalmefene is infused, another 1.0 mg dose of parenteral nalmefene may be given, such as by subcutaneous or intramuscular injection. Approximately 10 hours later a final intramuscular or subcutaneous bolus dose of nalmefene can be given, thereby completing a cycle of parenteral administration of nalmefene totaling approximately 4.0 mg over a span of time approximately 24 hours.

Alternatively, a loading dose of from about 0.5–1.5 mg to no more than about 1.5–2.0 mg is given, followed by slow intravenous infusion at a rate equivalent to 2.0–3.5 mg/day. This dosage regimen is convenient if the patient is to receive intravenous hydration for treatment of nausea and/or diarrhea as may sometimes be associated with withdrawal from opioids.

A method for treating the acute and severe diarrhea typically precipitated by rapid detoxification procedures is to administer the somatostatin analogue octreotide. While octreotide has proven effective in treating clinically significant diarrhea during rapid detoxification, it is associated with an unacceptable incidence of bradycardia, which in some instances has been so severe as to be life threatening.

It is, accordingly, an object of the invention to provide an effective method for treating acute and severe diarrhea.

It is a further object of the invention to provide such a method which reduces the incidence of life threatening bradycardia.

It is a still further object of the invention to provide a method of rapid narcotic detoxification which safely and effectively treats the acute and severe diarrhea typically accompanying acute withdrawal.

SUMMARY OF THE INVENTION

The present invention meets the above-stated objects by providing a method for treating acute and severe diarrhea comprising the step of administering octreotide in an amount sufficient to alleviate the diarrhea without precipitating clinically significant bradycardia. Preferably octreotide is administered in a dosage of from about 0.025 mg to about 0.1 mg and, more preferably, in a dose of about 0.0007 mg/kg of body weight. In the most preferred embodiment of the invention, the method comprises administering octreotide together with an anticholenergic such as atropine or glycopyrrolate.

The present invention also provides a method for rapidly detoxifying a patient addicted to exogenously administered narcotics while effectively treating the acute and severe diarrhea that typically accompanies acute withdrawal. According to the invention, acute clinical withdrawal is induced by administering at least about 0.5–1.5 mg up to about 1.5–2.0 mg of nalmefene, based on the weight of a 70 kg human. The diarrhea associated with such withdrawal is treated by administering octreotide in an amount sufficient to alleviate the diarrhea without precipitating clinically significant bradycardia. In the preferred embodiment octreotide is administered together with an anticholenergic, such as atropine or glycopyrrolate.

DETAILED DESCRIPTION OF THE INVENTION

The present invention will be described in detail in the context of a method for rapidly detoxifying a patient addicted to exogenously administered narcotics. However, it should be understood that the broader aspects of the invention are in no way limited in this regard. In particular, the method of treating acute and severe diarrhea disclosed herein is not limited to the diarrhea associated with acute withdrawal but, instead, is useful in treating clinically significant diarrhea generally, such as the diarrhea associated with chemotherapy.

A method of rapid detoxification as taught by the invention is conducted as follows. A patient addicted to narcotics undergoes intravenous cannulation by either the peripheral or central venous route, and the appropriate intravenous solution is infused intravenously at the required rate for the size and conditions of the patient. Monitors of life function are attached to the patient which may include a pulse oximeter, electrocardiogram patches, a blood pressure cuff attached to a sphygmomanometer and a means to measure the carbon dioxide of the patient's exhaled breath by way of capnography.

A medication to induce unconsciousness is administered, preferably by the intravenous route, in doses appropriate for the patient's weight and medical condition. This medication should be a non-opioid derivative not related to the narcotic classification of drugs, such as midazolam, propofol, sodium pentothal, a combination thereof, or other drugs commonly used to induce unconsciousness. As a specific example, a dose of 0.3 milligrams of midazolam per kilogram of body weight administered intravenously is usually sufficient to produce unconsciousness.

This is typically followed by intravenous administration of a medication such as a depolarizing or non-depolarizing neuromuscular blocking agent to facilitate intubation of the patient's trachea. The endotracheal tube is then secured in the correct anatomic position using usual anesthetic care measures. After stabilization of the patient's life functions as usually done in routine anesthetic management, the patient is administered parenterally about 0.025 mg to about 0.1 mg octreotide, preferably about 0.0007 mg/kg of body weight. This dosage of octreotide is sufficient to prevent the acute and severe diarrhea which frequently accompanies acute detoxification and does not precipitate significant bradycardia. Administering octreotide in this dosage range also does not result in the abdominal distention that is frequently observed at higher dosage levels of octreotide.

Clinical evidence establishes that the incidence of bradycardia which accompanies octreotide administration can be further reduced by combining the above-specified octreotide dosage with an anticholenergic such as atropine or glycopyrrolate. As noted previously, glycopyrrolate is preferred and is administered parenterally with the octreotide in an amount ranging from about 0.2 mg to about 0.4 mg glycopyrrolate. However, from about 0.2 mg to about 0.4 mg atropine administered parenterally is also effective.

After octreotide and glycopyrrolate have been administered and the patient's vital signs are stable, nalmefene is administered parenterally, preferably by intravenous route. For a 70 kilogram adult patient, the typical initial dose of parenteral nalmefene is from about 0.5–1.5 mg to no more than about 1.5–2.0 mg of nalmefene. The dosage is adjusted proportionally based on the weight of the patient, and the rate of administration of nalmefene may be titrated upward or downward depending on the response of the patient's sympathetic nervous system as evidence by monitoring of life functions and other clinical criteria. Some time thereafter, usually no more than four hours after said administration of nalmefene is complete, the patient can be expected to be detoxified and can be safely rendered back to a state of consciousness. Upon awakening the acute phase of withdrawal will have been completed.

In a second embodiment of this aspect of the invention, the patient is administered a glucocorticoid either prior to or after anesthetization. Acute withdrawal produces an "Addisonian-like" state due to the patient's decreased ability to secrete stress hormones in response to the physiological stress imposed by acute withdrawal. The administration of a glucocorticoid prior to inducing withdrawal assists the patient in mounting an appropriate stress response and therefore further alleviates the acute and severe diarrhea and other "Addisonian-like" signs and symptoms which accompanies rapid detoxification.

The preferred glucocorticoid is hydrocortisone, although it should be understood that the invention is not limited in this regard. Other glucocorticoids well known to those skilled in the art as providing similar pharmacological effects may also be utilized. Hydrocortisone is administered in an amount of from about 25 mg to about 100 mg. It has been clinically established that hydrocortisone is particularly effective in reducing the symptoms of acute withdrawal, such as severe diarrhea, when it is combined with diphenhyramine and ranitidine. Accordingly, at about the time of being anesthetized the patient is given an intravenous infusion of hydrocortisone in the above-specified dosage, from about 10 mg to about 100 mg diphenhydramine or equivalent dose of other H1 histamine receptor blocker, and from about 10 mg to about 100 mg ranitidine or equivalent dose of other H2 histamine receptor blocker. The preferable doses for a 70 kg human are 50 mg diphenhydramine and 50 mg ranitidine.

During the post-detoxification period, the patient may be given an antidiarrheal to alleviate loose stool and diarrhea which frequently accompanies the acute reaction of withdrawal from opioid drugs. The antidiarrheal loperimide is preferred and is administered enterally in a dosage of from about 4 mg to about 16 mg per day. Alternatively, octreotide administered parenterally in a dose of from about 0.025 mg to about 0.05 mg every 12 hours, preferably 0.0007 mg/kg of body weight every 12 hours, will effectively treat symptoms of diarrhea without causing significant bradycardia. Octreotide is a particularly effective treatment when combined with an anticholinergic such as glycopyrrolate in a preferred dose of from about 0.2 mg to about 0.4 mg, in the days following detoxification.

As noted previously, octreotide administered in the above-described dosage range is also an effective treatment for the severe diarrhea which is typically present in other clinical situations, such as patients who are undergoing chemotherapy treatment. As noted above, octreotide is a particularly effective treatment for acute and severe diarrhea when combined with an anticholenergic such as atropine or, more preferably, glycopyrrolate. Thus, the dosage of octreotide is combined with from about 0.2 mg to about 0.4 mg of glycopyrrolate in the preferred method of treating severe diarrhea.

Accordingly, a method for treating acute and severe diarrhea has been disclosed. In addition, a method for rapidly detoxifying a patient addicted to narcotics has also been disclosed, wherein the acute and severe diarrhea typically accompanies acute withdrawal is eliminated without precipitating significant bradycardia or abdominal bloating. While preferred embodiments of these treatment methods have been disclosed, various modifications and substitutions may be made without departing from the spirit and scope of the invention. Accordingly, it is to be understood that the present invention has been described by way of example and not by limitation.

I claim:

1. A method for rapidly detoxifying a patient addicted to narcotic said method comprising the steps of:
   (a) anesthetizing the patient by inducing unconsciousness;
   (b) administering octreotide in a dosage of from about 0.025 mg to about 0.1 mg, which is an amount sufficient to alleviate acute and sever diarrhea without precipitating clinically significant bradycardia; and
   (c) inducing acute clinical withdrawal by administering nalmefene.

2. The method of claim 1, where octreotide is administered parenterally in a dosage of from about 0.025 mg to about 0.1 mg.

3. The method of claim 2, wherein step (b) is further characterized in that octreotide is administered together with an anticholenergic compound.

4. The method of claim 3, wherein the anticholenergic is glycopyrrolate.

5. The method of claim 4, wherein glycpyrrolate is administered in a dosage of from about 0.2 mg to about 0.4 mg.

6. The method of claim 1, further comprising the step of:
   (d) administering an antidiarrheal to alleviate loose stool and diarrhea during the period following rapid detoxification.

7. The method of claim 6, wherein the antidiarrheal is selected from the group consisting of loperimide and the combination of 0.025 mg to about 0.1 mg octreotide and from about 0.2 to about 0.4 mg glycopyrrolate.

8. The method of claim 1, wherein prior to step (c), the method further includes the step of administering a glucocorticoid to the patient.

9. The method of claim 8, wherein the glucocorticoid is hydrocortisone.

10. The method of claim 9, wherein the hydrocortisone is administered in a dosage of from about 25 mg to about 100 mg.

11. The method of claim 8, wherein the step of administering the glucocorticoid is further characterized in that diphenhydramine and ranitidine are administered together with the glucocorticoid.

12. The method of claim 1, wherein step (c) is further characterized in that nalmefene is administered in a dosage of from about 0.5–1.5 mg to no more than about 1.5–2.0 mg based on the weight of a 70 kg patient.

13. A method for rapidly detoxifying a patient addicted to narcotics, said method comprising the steps of:
   (a) anesthetizing the patient by inducig unconsciousness;
   (b) administering octreotide in a dosage of from about 0.025 mg to about 0.1 mg together with glycopyrrolate in a dosage of from about 0.2 mg to about 0.4 mg; and
   (c) inducing acute clinical withdrawal by administering nalmefene in a dosage of from about 0.5–1.5 mg to no more than about 1.5–2.0 mg, based on the weight of a 70 kg patient.

14. The method of claim 13 further including the step of:
   (d) administering an antidiarrheal to alleviate symptoms of loose stool and diarrhea in the period following rapid detoxification.

15. The method of claim 13, wherein prior to step (a), the method further includes the step of administering a glucocorticoid to the patient.

16. A method for rapidly detoxifying a patient addicted to narcotics, said method comprising the steps of:
   (a) anesthetizing the patient by inducing unconsciousness;
   (b) administering octreotide in a dosage of from about 0.025 mg to about 0.1 mg together with glycopyrrolate in a dosage of from about 0.2 mg to about 0.4 mg; and
   (c) inducing acute clinical withdrawal by administering nalmefene.

\* \* \* \* \*